(12) United States Patent
Tong et al.

(10) Patent No.: US 11,281,801 B2
(45) Date of Patent: Mar. 22, 2022

(54) DECENTRALIZED PRIVACY-PRESERVING CLINICAL DATA EVALUATION

(71) Applicant: INTERNATIONAL BUSINESS MACHINES CORPORATION, Armonk, NY (US)

(72) Inventors: Sui Jun Tong, Beijing (CN); Wen Sun, Beijing (CN); Yi Qin Yu, Beijing (CN); Eryu Xia, Beijing (CN); Yong Qin, Beijing (CN)

(73) Assignee: International Business Machines Corporation, Armonk, NY (US)

(*) Notice: Subject to any disclaimer, the term of this patent is extended or adjusted under 35 U.S.C. 154(b) by 357 days.

(21) Appl. No.: 16/238,216

(22) Filed: Jan. 2, 2019

(65) Prior Publication Data

US 2020/0210621 A1 Jul. 2, 2020

(51) Int. Cl.
| | |
|---|---|
| H04L 29/06 | (2006.01) |
| G06F 21/62 | (2013.01) |
| G06F 21/60 | (2013.01) |
| G06N 20/00 | (2019.01) |
| G06F 16/28 | (2019.01) |

(52) U.S. Cl.
CPC ........ G06F 21/6254 (2013.01); G06F 16/285 (2019.01); G06F 21/602 (2013.01); G06N 20/00 (2019.01); H04L 2209/38 (2013.01)

(58) Field of Classification Search
CPC .. G06F 21/6254; G06F 21/602; G06F 16/285; G06N 20/00; H04L 2209/38; G16H 40/60; G16H 50/70; G16H 10/20
See application file for complete search history.

(56) References Cited

U.S. PATENT DOCUMENTS

| | | | |
|---|---|---|---|
| 7,627,652 B1 * | 12/2009 | Commons ........... | H04L 67/1097 709/213 |
| 2011/0249899 A1* | 10/2011 | Wu ....................... | G06K 9/6211 382/190 |

(Continued)

FOREIGN PATENT DOCUMENTS

WO WO2013010569 * 1/2013

OTHER PUBLICATIONS

Nabiha et al. "New Dynamic Ensemble of Classifiers Selection Approach Based on Confusion matrix for Arabic Handwritten recognition", 2012 International Conference on Multimedia Computing and Systems, p. 308-313 (Year: 2012).*

(Continued)

*Primary Examiner* — Taghi T Arani
*Assistant Examiner* — Lin Chang
(74) *Attorney, Agent, or Firm* — Tutunjian & Bitetto, P.C.; Joseph Petrokaitis (57) ABSTRACT

A system for decentralized privacy-preserving clinical data evaluation includes a plurality of sites of a decentralized private network, a memory device for storing program code, and at least one processor device operatively coupled to the memory device and configured to execute program code stored on the memory device to, for each of the local datasets, evaluate the local dataset using each of the local models to obtain one or more features related to a degree of outlierness, determine at least one outlier dataset based on the one or more features, and implement one or more actions based on the determination.

20 Claims, 6 Drawing Sheets

(56) References Cited

U.S. PATENT DOCUMENTS

| | | | | |
|---|---|---|---|---|
| 2013/0254536 | A1* | 9/2013 | Glover | G06F 21/6209 |
| | | | | 713/165 |
| 2015/0195254 | A1* | 7/2015 | Stiglic | H04L 9/0825 |
| | | | | 713/171 |
| 2016/0182240 | A1* | 6/2016 | Nayshtut | H04L 63/0815 |
| | | | | 713/158 |
| 2016/0232457 | A1* | 8/2016 | Gray | G06T 11/206 |
| 2016/0260187 | A1* | 9/2016 | Rajagopalan | G06Q 40/06 |
| 2017/0060124 | A1* | 3/2017 | Hara | G05B 23/0221 |
| 2017/0103167 | A1 | 4/2017 | Shah | |
| 2017/0103472 | A1 | 4/2017 | Shah | |
| 2017/0344903 | A1* | 11/2017 | Hackett | G06N 20/10 |
| 2018/0018590 | A1* | 1/2018 | Szeto | G06F 21/6254 |
| 2018/0211059 | A1 | 7/2018 | Aunger et al. | |
| 2018/0218779 | A1* | 8/2018 | Collins, Jr. | G16H 10/60 |
| 2018/0237026 | A1* | 8/2018 | Chowdhury | G07C 5/008 |
| 2018/0315143 | A1* | 11/2018 | Rang | G06N 5/04 |
| 2019/0272764 | A1* | 9/2019 | Thomas | G09B 7/02 |
| 2020/0012763 | A1* | 1/2020 | Arngren | H04L 9/14 |

OTHER PUBLICATIONS

Marom et al. "Using the Confusion Matrix for Improving Ensemble Classifiers", 2010 IEEE 26-th Convention of Electrical and Electronics Engineers in Israel, p. 555-559. (Year: 2010).*

Xiong et al. "Direct Robust Matrix Factorization for Anomaly Detection", IEEE 11th International conference on data mining, 2011 (Year: 2011).*

Du et al. "Robust Local Outlier Detection", IEEE 15th International Conference on Data Mining workshops, 2015 (Year: 2015).* https://www.fda.gov/scienceresearch/specialtopics/realworldevidence/default.htm, Dec. 19, 2018.

https://www.fda.gov/downloads/MedicalDevices/DeviceRegulationandGuidance/GuidanceDocuments/UCM513027.pdf Aug. 31, 2017, U.S. Department of Health and Human Services Food and Drug Administration, Center for Devices and Radiological Health, Center for Biologies Evaluation and Research.

S. Peddicord, https://www.fda.gov/NewsEvents/Newsroom/FDAInBrief/ucm625228.htm, Nov. 6, 2018.

https://www.fda.gov/Drugs/ScienceResearch/ucm624785.htm, Nov. 6, 2018.

* cited by examiner

DECENTRALIZED PRIVACY-PRESERVING CLINICAL DATA EVALUATION

BACKGROUND

Technical Field

The present invention generally relates to machine learning, and more particularly to decentralized privacy-preserving clinical data evaluation.

Description of the Related Art

One goal of medical organizations or entities (e.g., hospitals) is to collect and evaluate high-quality clinical data for clinical research tasks. However, privacy-preservation steps may need to be taken within a network including a plurality of entities to ensure anonymity of the source entity of clinical data during evaluation.

SUMMARY

In accordance with an embodiment of the present invention, a system for decentralized privacy-preserving clinical data evaluation is provided. The system includes a plurality of sites of a decentralized private network. The plurality of sites are associated with respective medical entities, and each of the plurality of sites includes a local database maintaining a local dataset including a partition of a clinical dataset, chaincode configured to communicate with an ordering service of the decentralized private network and implement model construction and dataset score computing, and a ledger maintaining a local model trained based on a local dataset to preserve anonymity of the corresponding medical entity. The system further includes a memory device for storing program code and at least one processor operatively coupled to the memory device. The at least one processor is configured to execute program code stored on the memory device to, for each of the local datasets, evaluate the local dataset using each of the local models to obtain one or more features related to a degree of outlierness, determine at least one outlier dataset based on the one or more features, and implement one or more actions based on the determination.

In accordance with another embodiment of the present invention, a computer-implemented method decentralized privacy-preserving clinical data evaluation is provided. The method includes obtaining, from each of a plurality of sites of a decentralized private network, a local model trained based on a local dataset including a partition of a clinical dataset, the plurality of sites being associated with respective medical entities. Each of the plurality of sites includes a local database maintaining its local dataset, chaincode configured to communicate with an ordering service of the decentralized private network and implement model construction and dataset score computing, and a ledger maintaining the local model to preserve anonymity of the corresponding medical entity. The method further includes, for each of the local datasets, evaluating the local dataset using each of the local models to obtain one or more features related to a degree of outlierness, determining at least one outlier dataset based on the one or more features, and implementing one or more actions based on the determination.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

The embodiments described herein provide for systems and methods for implementing a decentralized privacy-preserving clinical data evaluation network. For example, clinical datasets from a plurality of medical entities can be stored at a plurality of sites of a decentralized private network, e.g., a private blockchain network, to prevent source data (e.g., raw data) from being directly accessed by others. For example, the plurality of medical entities can include one or more medical organizations (e.g., one or more hospitals). The embodiments described herein can protect the privacy of clinical datasets stored at the plurality of medical entities, thereby allowing the plurality of medical entities to freely share clinical data among each other in a privacy-preserving manner. Sharing the clinical data in accordance with embodiments described herein can accelerate clinical research processes performed by the plurality of medical entities by eliminating outlier datasets for a clinical research task to improve data quality, thereby reducing waste in both time and money.

Illustratively, the clinical datasets can include real-world data (RWD). RWD can include data obtained from sources associated with patient outcomes in real-world settings (e.g., patient data, clinical trials and observational cohort studies). RWD can be obtained from electronic health records (EHR), claims and billing activity databases, product and disease registries, patient-generated data including in home-use settings, data obtained from electronic devices (e.g., mobile devices) providing information on health status, etc. RWD can be used to derive real world evidence (RWE), which can include evidence regarding safety and efficacy of a medical product (e.g., drug or device). That is, RWE can be used by entities to make decisions about medical product suitability. Such RWD and RWE can be used to determine the optimal use of a medical product in real-world environments and with respect to patient cohorts likely to be treated once the medical product is produced. Such RWD/RWE can be implemented to build a machine learning model pertaining to medical science (e.g., predicting medical risk), be transmitted for display on a computing device of a doctor for use in treating patients, etc.

Figure 1:
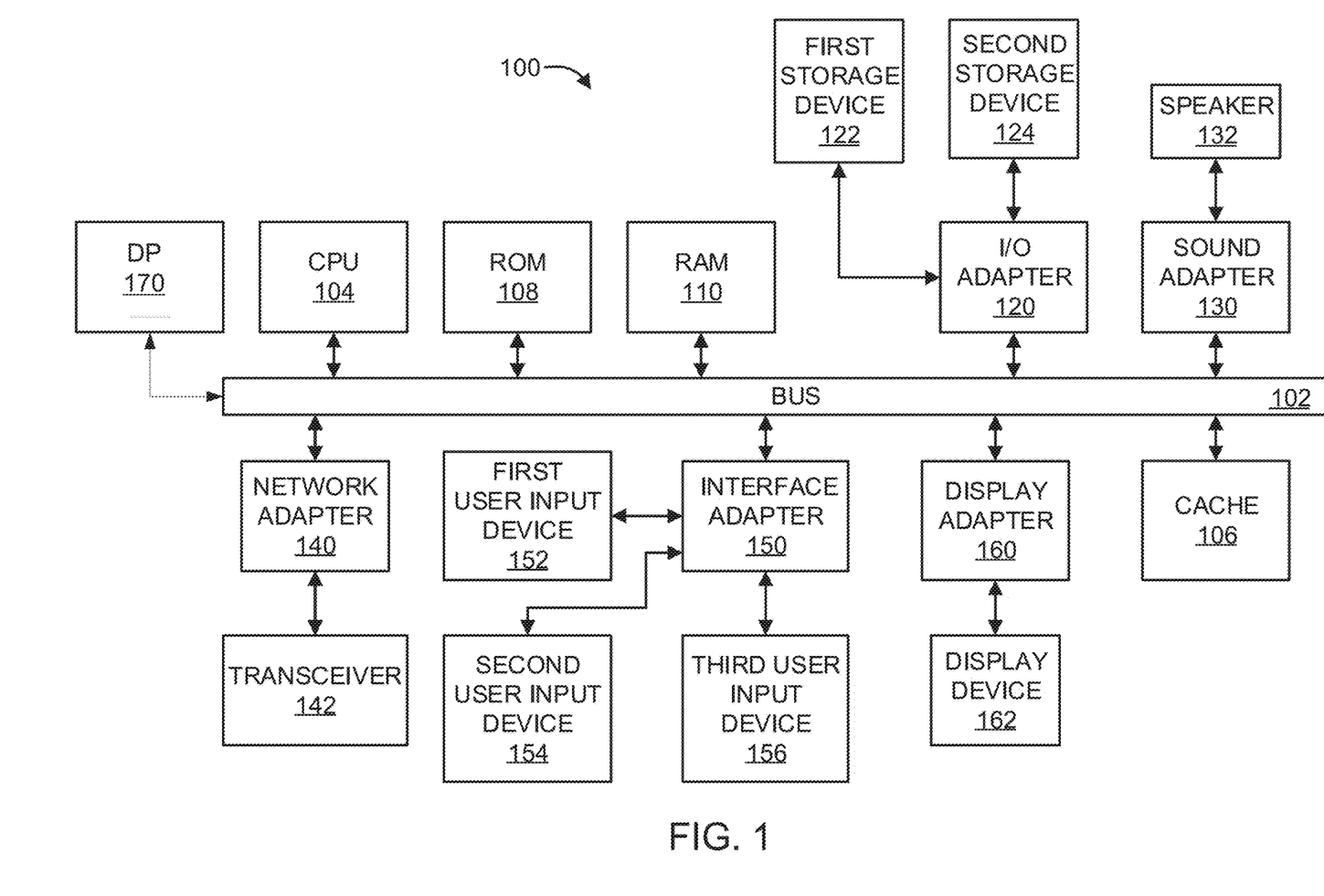
FIG. 1 is a block diagram of a processing system, in accordance with an embodiment of the present invention.

Referring now to the drawings in which like numerals represent the same or similar elements and initially to FIG. 1, an exemplary processing system 100 to which the present invention may be applied is shown in accordance with one embodiment. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

Data privacy (DP) component 170 may be operatively coupled to system bus 102. DP component 170 is configured to perform one or more of the operations described below for implementing a decentralized privacy-preserving clinical data evaluation network. DP component 170 can be implemented as a standalone special purpose hardware device, or may be implemented as software stored on a storage device. In the embodiment in which DP component 170 is software-implemented, although shown as a separate component of the computer system 100, DP component 170 can be stored on, e.g., the first storage device 122 and/or the second storage device 124. Alternatively, DP component 170 can be stored on a separate storage device (not shown).

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 2:
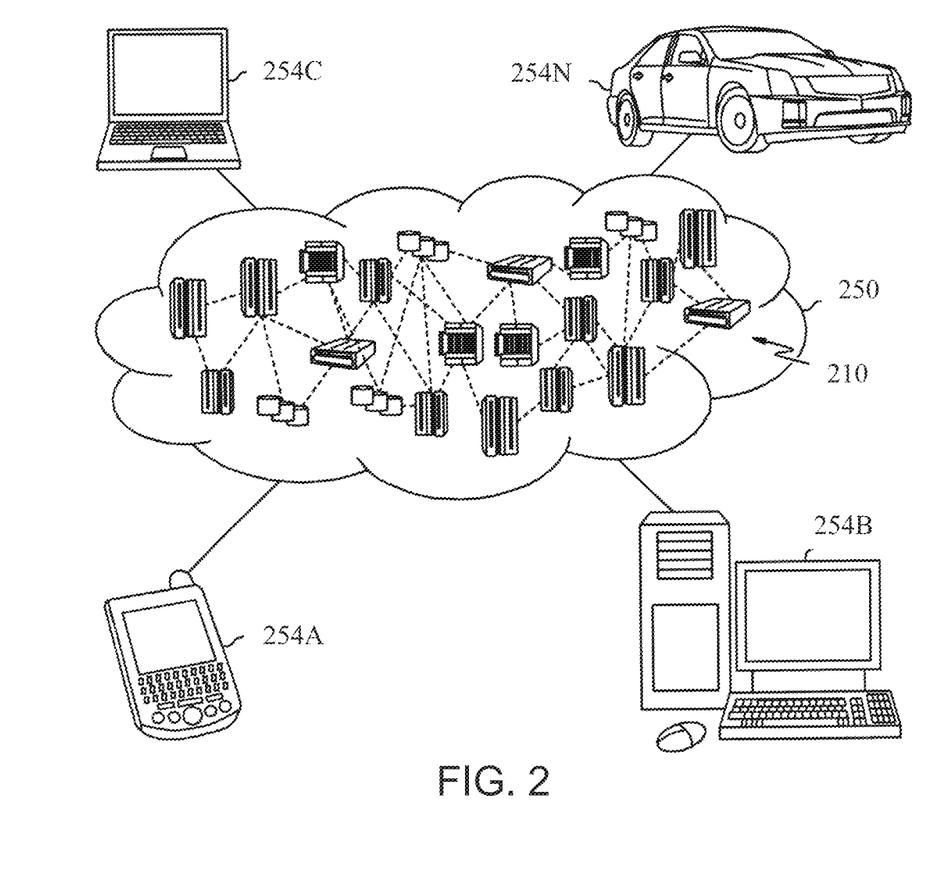
FIG. 2 is a block diagram showing an illustrative cloud computing environment having one or more cloud computing nodes with which local computing devices used by cloud consumers communicate, in accordance with an embodiment of the present invention.

Referring now to FIG. 2, illustrative cloud computing environment 250 is depicted. As shown, cloud computing environment 250 includes one or more cloud computing nodes 210 with which local computing devices used by cloud consumers, such as, for example, personal digital assistant (PDA) or cellular telephone 254A, desktop computer 254B, laptop computer 254C, and/or automobile computer system 254N may communicate. Nodes 210 may communicate with one another. They may be grouped (not shown) physically or virtually, in one or more networks, such as Private, Community, Public, or Hybrid clouds as described hereinabove, or a combination thereof. This allows cloud computing environment 150 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
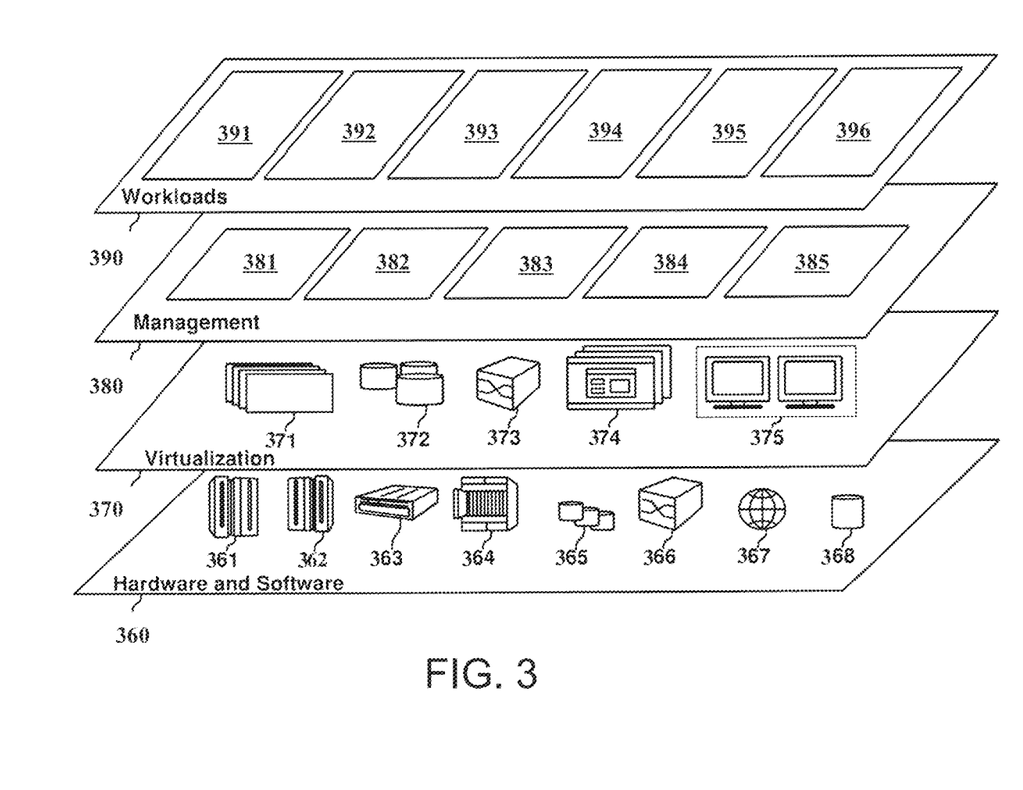
FIG. 3 is a block diagram showing a set of functional abstraction layers provided by a cloud computing environment, in accordance with an embodiment of the present invention.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and Pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395; and privacy management 396.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

To the extent the embodiments described herein collect, store, or employ personal information provided by, or obtained from, individuals (for example, current locations of drivers, historical records of drivers, etc.), such information shall be used in accordance with all applicable laws concerning protection of personal information. Additionally, the collection, storage, and use of such information may be subject to consent of the individual, i.e., user, to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

Figure 4:
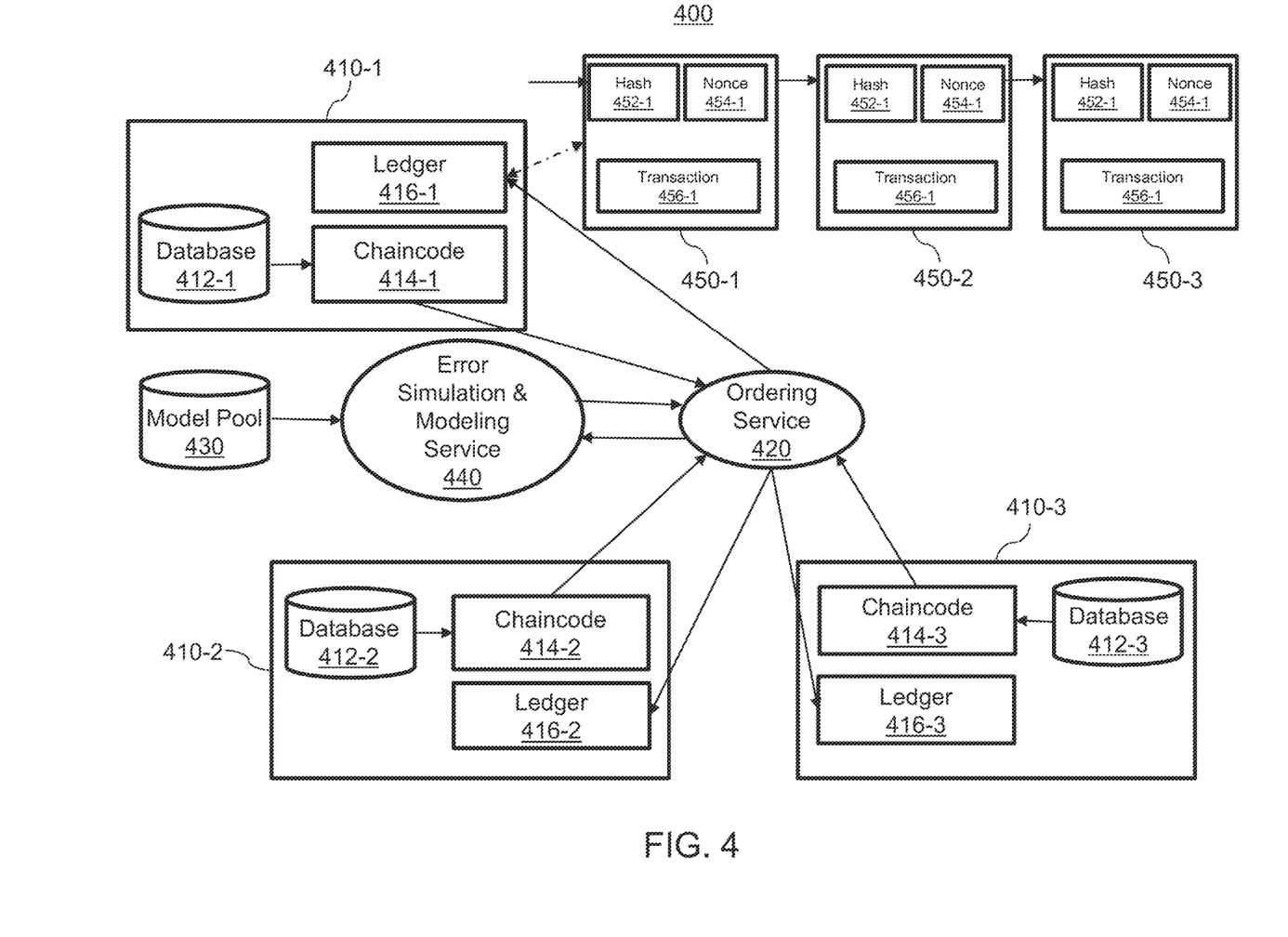
FIG. 4 is a block diagram of a system for implementing a decentralized privacy-preserving clinical data evaluation network, in accordance with an embodiment of the present invention.

With reference to FIG. 4, a block diagram is provided illustrating a system 400 for decentralized privacy-preserving clinical data evaluation. The system 400 includes a decentralized private network. In this illustrative embodiment, the decentralized private network includes a blockchain network. However, any suitable decentralized private network can be employed in accordance with the embodiments described herein.

As shown, the system includes a plurality of sites 410-1 through 410-3, an ordering service 420, a model pool 430, an error simulation & modeling service 440, and blocks 450-1 through 450-3 forming a chain. Each block 450-1 through 450-3 represents an ordered set of transactions that is cryptographically linked to the preceding block. As shown, block 450-1 can include hash data 452-1, nonce data 454-1 and transaction data 456-1, block 450-2 can include hash data 452-2, nonce data 454-2 and transaction data 456-2, and block 450-3 can include hash data 452-3, nonce data 454-3 and transaction data 456-3.

The sites 410-1 through 410-3 are participants (e.g., members) of the blockchain network. In one embodiment, the sites 410-1 through 410-3 correspond to a plurality of medical organizations or entities (e.g., hospitals). Although three site nodes are shown in this illustrative example, any number of site nodes can be included in the system 400 in accordance with the embodiments described herein. Other participants of the blockchain network (e.g., users) (not shown) can be included.

The site 410-1 includes a local database 412-1, chaincode 414-1 and a ledger 416-1, the site node 410-2 includes a local database 412-2, chaincode 414-2 and a ledger 416-2, and the site node 410-3 includes a local database 412-3 chaincode 414-3 and a ledger 416-3.

Each local database 412-1 through 412-3 can store local datasets. In one embodiment, the local datasets include real-world data (RWD). RWD can include data obtained from sources associated with patient outcomes in real-world settings (e.g., patient data, clinical trials and observational cohort studies). RWD can be obtained from electronic health records (EHR), claims and billing activity databases, product and disease registries, patient-generated data including in home-use settings, data obtained from electronic devices (e.g., mobile devices) providing information on health status, etc.

Each chaincode 414-1 through 414-3 can include a set of functions to query or update the ledger. For example, each chaincode 414-1 through 414-3 can include a set of functions to implement model construction and dataset score computing, in accordance with the embodiments described herein.

The ordering service 420 of the blockchain network provides a communication channel for the system 400 that collects transactions from the site nodes 410-1 through 410-3, orders the transactions, and bundles the transactions into blocks. The ordering service 420 can then distribute the new blocks to peers (not shown), which then verify the blocks. The ordering service 420 can include the cryptographic identity material that is tied to each member and authenticates the identity of clients and peers to access the network. The ledgers 416-1 through 416-3 can maintain data output by the ordering service 420.

The model pool 430 can collect and store reference models and associated datasets. The reference models can include existing, well-established models that have been built from respective datasets. The error simulation & modeling service 440 can select a reference model from the model pool 430 based on a target model, and perform error simulation and classifier training based on the selected reference model. Each of the sites 410-1 through 410-3 can train a local model based on local datasets maintained on the local database 412-1 through 410-3, respectively. For example, each local model can be trained based on the reference model and the corresponding local dataset. The local datasets can include respective partitions of a clinical dataset. The local models can be submitted to the ledgers 416-1 through 416-3, respectively, for sharing among the site nodes 410-1 through 410-3 in a manner that preserves anonymity of the medical entities corresponding to the sites 410-1 through 410-3.

The local models and the local datasets can be used to improve data quality within the decentralized private network. For each of the local datasets, the local dataset can be evaluated using each of the local models to obtain one or more features related to a degree of outlierness. At least one outlier dataset is determined based on the one or more features, and one or more actions are implemented to address the at least one outlier dataset.

Further details regarding the operation and components of the system 400 will be described below with reference to FIG. 5.

Figure 5:
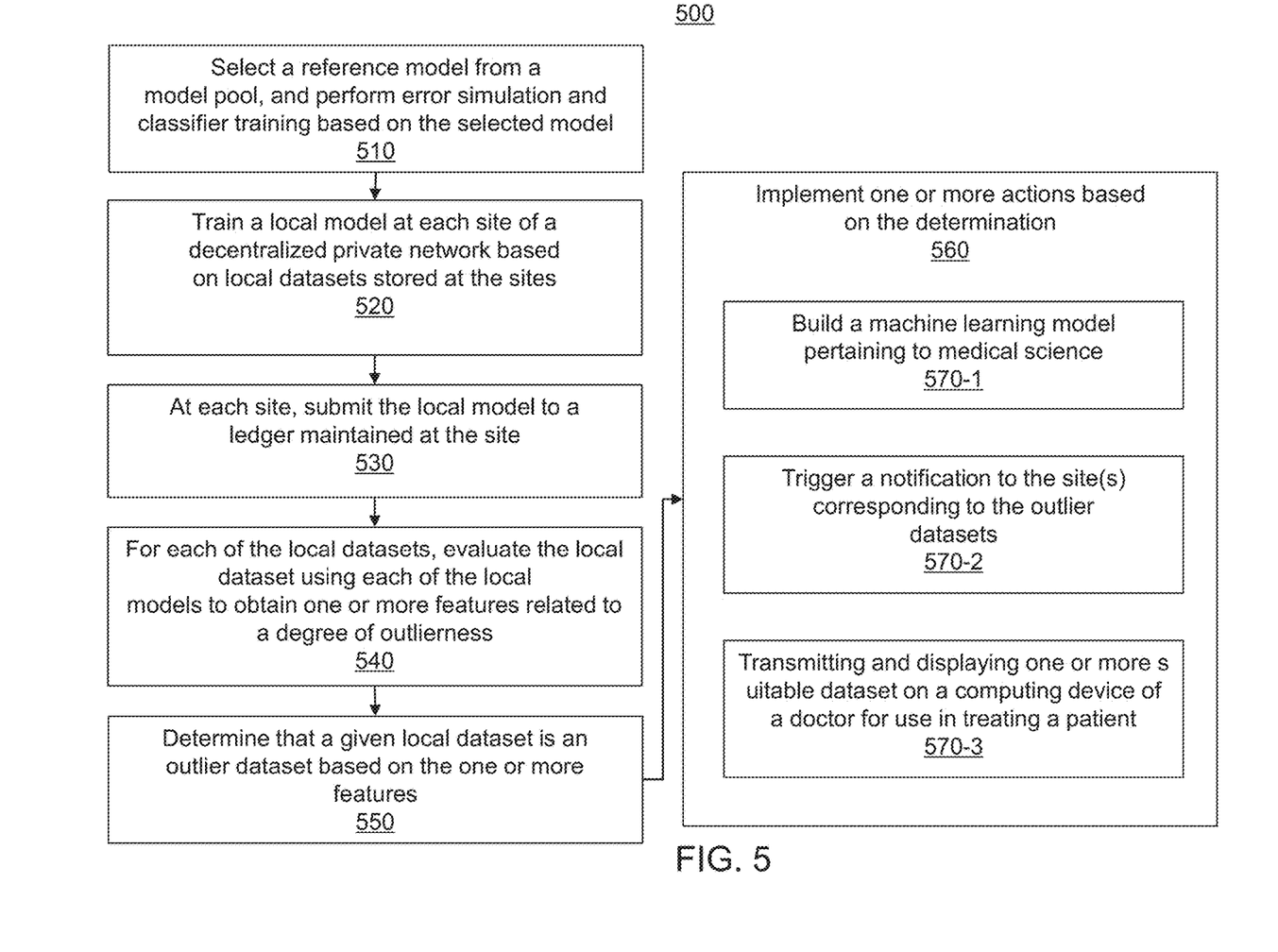
FIG. 5 is a block/flow diagram of a system/method for implementing a decentralized privacy-preserving clinical data evaluation network, in accordance with an embodiment of the present invention.

With reference to FIG. 5, a block/flow diagram is provided illustrating a system/method 500 for decentralized privacy-preserving clinical data evaluation. It is assumed that the process implemented by the system/method 500 is performed upon receiving a modeling task (e.g., a task for building a risk prediction model). The system/method 500 can be performed within the context of a decentralized private network, such as, e.g., the blockchain network described above with reference to FIG. 4.

At block 510, a reference model is selected from a model pool, and error simulation and classifier training is performed based on the selected model. The model pool can include a plurality of models and associated respective datasets. The plurality of models can include existing, well-established models. For example, given a target model M (F,O), where F denotes a feature set, O denotes an outcome and D denotes an associated dataset, a reference model M' (F', O') having an associated dataset D' most similar to the target model M can be selected from the model pool. In one embodiment, the reference model M' (F', O') can be a model selected from the model pool having a feature set F' that is a superset of F, and an outcome O' closest to O. For example, the associated dataset D' can be randomly partitioned into N subsets.

Regarding error simulation, error simulation can include simulating possible data errors in a given number of rounds. Typical errors can be simulated (e.g., randomly faked values) on different partitions. For example, for each of the rounds, no more than K subsets can be randomly selected, and a number of errors can be simulated on the selected subsets (note that errors will only be applied to data in F). Then, an error matrix E' for the selected reference model M' can be calculated.

Regarding classifier training, the error matrix E' can be used to train a classifier C. The classifier C can be obtained via supervised learning. As will be described in further detail, the classifier C can be applied to an error matrix E corresponding to the target model M to determine whether any outlier datasets exist.

Block 510 can be implemented by an error simulation & modeling service of the decentralized private network in communication with an ordering service of the decentralized private network, as described above with reference to FIG. 4.

As an illustrative example of the operations performed at block 510, let target model M be a logistic regression model used to predict a stroke event for in-hospital patients with variables (e.g., age, gender, days of stay), and let reference model M' be another logistic regression model used to predict a heart failure event for in-hospital patients with variables (e.g., age, gender, days of stay, diagnosis). An example of a dataset D' associated with the reference model M' is shown by the following table:

TABLE 1

| ID # | Label | Age | Gender | Days of stay | Diagnosis |
|---|---|---|---|---|---|
| 1 | 0 | 60 | M | 20 | I90 |
| 2 | 1 | 75 | F | 5 | D01 |
| 3 | 0 | 55 | F | 11 | M03 |
| 4 | 0 | 62 | F | 2 | H08 |
| 5 | 0 | 48 | M | 9 | E01 |
| 6 | 1 | 71 | F | 16 | I03 |
| 7 | 0 | 82 | F | 35 | E02 |
| 8 | 0 | 67 | M | 17 | I90 |
| 9 | 1 | 79 | M | 6 | H05 |

Assuming that there are n sites of the decentralized private network $s_1, s_2, \ldots, s_n$, the dataset D' can be partitioned into n partitions corresponding to respective ones of the n sites. One or more of the n sites can correspond to a medical organization or entity (e.g., hospital). In this illustrative example, n=3 (e.g., as described above with reference to FIG. 4), with the data corresponding to ID #s 1-3 being assigned to site $s_1$, the data corresponding to ID #s 4-6 being assigned to site $s_2$, and the data corresponding to ID #s 7-9 being assigned to site $s_3$. Then, typical errors can be simulated for suspicious sites (e.g., sites having outlier datasets). For example, the following table illustrates a simulation assuming that site $s_1$ is a suspicious site that uses a faked fixed value in the "days of stay" variable:

TABLE 2

| ID # | Label | Age | Gender | Days of stay | Diagnosis |
|---|---|---|---|---|---|
| 1 | 0 | 60 | M | 7 | I90 |
| 2 | 1 | 75 | F | 7 | D01 |
| 3 | 0 | 55 | F | 7 | M03 |
| 4 | 0 | 62 | F | 2 | H08 |
| 5 | 0 | 48 | M | 9 | E01 |
| 6 | 1 | 71 | F | 16 | I03 |
| 7 | 0 | 82 | F | 35 | E02 |
| 8 | 0 | 67 | M | 17 | I90 |
| 9 | 1 | 79 | M | 6 | H05 |

Generally, local reference models $M_1'$ through $M_n'$ can be trained at respective ones of the sites $s_1$ through $s_n$ and evaluated by each site. In this illustrative example, a local reference model $M_1'$ can be trained on a local dataset for site $s_1$, a local reference model $M_2'$ can be trained on a local dataset for site $s_2$, and a local reference model $M_3'$ can be trained on a local dataset for site $s_3$. The local reference models $M_1'$ through $M_3'$ can then be applied to each of the sites $s_1$ through $s_3$ for local reference model evaluation. The local reference model evaluation can be based on error rate. In general, an n×n error matrix E' can be generated based on the error calculation, where n refers to the number of sites, and where entry $E_{ij}'$ is the evaluation of model $M_i'$ on site $s_j$. In this illustrative example, a 3×3 error matrix E' can be generated as follows:

TABLE 3

| 0.1 | 0.4 | 0.5 |
| 0.4 | 0.2 | 0.3 |
| 0.4 | 0.2 | 0.2 |

For a site $s_i$, the relevant errors can be calculated as ($\Sigma_{j=1}^{n} \Sigma_{ij}'$, $\Sigma_{j=1}^{n} \Sigma_{ji}'$). One or more features related to the degree of outlierness can then be obtained based on the error matrix E'. For example, the following matrix corresponding to outlierness can be then obtained to train a classifier C that can be used classify whether any of the sites $s_1$ through $s_3$ have an outlier dataset:

TABLE 4

| Site | $D_1$ | $D_2$ | Max | Min | Avg | Sum | Label |
|---|---|---|---|---|---|---|---|
| $s_1$ | 0.5 | 0.425 | 0.5 | 0.1 | 0.36 | 1.8 | 1 |
| $s_2$ | 0.224 | 0.2 | 0.4 | 0.2 | 0.3 | 1.5 | 0 |
| $s_3$ | 0.2 | 0.316 | 0.5 | 0.2 | 0.32 | 1.6 | 0 |

Here, $D_1$ refers to a first distribution of errors of a given one of the local reference models $M_i'$ on different ones of the local datasets $ds_j$, $D_2$ refers to a second distribution of errors of a given one of the local reference models $M_i'$ on different ones of the local datasets $ds_j$, Max is the maximum of the relevant errors, Min is the minimum of the relevant errors, average is the average value of the relevant errors, and Sum is the summation of the relevant errors. The first distribution of errors and the second distribution of errors can be determined as follows:

$$D_{i1} = \sqrt{\sum_{j=1}^{n} (E_{ij}' - E_{ii}')^2}$$

$$D_{i2} = \sqrt{\sum_{j=1}^{n} (E_{ji}' - E_{ii}')^2}$$

At block 520, local models are trained at each site of the decentralized private network based on local datasets stored at the sites. As mentioned above, one or more of the sites can correspond to a medical organization or entity (e.g., hospital). Each local dataset corresponds to a partition of a clinical dataset. For example, each site $s_i$ can store a local dataset $ds_i$, and each site $s_i$ can train a local model $M_i$ (i=1, 2, . . . , n) in an attempt to locally build the target model M using its local dataset $ds_i$.

At block 530, at each site, the local model is submitted to a ledger maintained at the site. Submitting the local model to the ledger can preserve anonymity of the entity corresponding to the site. This can prevent each of the entities from knowing the source of the data.

At block 540, for each of the local datasets, the local dataset is evaluated using each of the local models to obtain one or more features related to a degree of outlierness. For example, each of the sites can have access to the local models for evaluation purposes, and can use their local datasets to evaluate the performance of all of the local models.

In one embodiment, evaluating the local dataset includes calculating an error matrix based on an application of each of the local models to the local dataset. For example, an n×n error matrix $E_{ij}$ can be represented by the following matrix, where n refers to the number of sites, and entry $E_{ij}$ corresponds to the model $M_i$ locally trained at site i applied to the local dataset associated with site j:

TABLE 5

| $E_{11}$ | $E_{12}$ | ... | $E_{1n}$ |
|---|---|---|---|
| $E_{21}$ | $E_{22}$ | ... | $E_{2n}$ |
| ... | ... | ... | ... |
| $E_{n1}$ | $E_{n2}$ | ... | $E_{nn}$ |

For example, similar to the discussion at block 510 with respect to the local reference models, a 3×3 error matrix E can be calculated based on the local models. One or more features related to a degree of outlierness (e.g., $D_1$, $D_2$, Max, Min, Avg, and Sum) for each site $s_i$ can be calculated from the error matrix E, similar to the manner described above at block 510 with respect to the local reference models.

At block 550, it is determined that a given local dataset is an outlier dataset based on the one or features. In one embodiment, hierarchical clustering can be applied to the error matrix E to filter out obvious outliers prior to the determination. The classifier C trained at block 510 can then be applied to the one or more features to determine whether a local dataset in a certain site is an outlier. Outlier local datasets can have quite a different error distribution with other ones of the local datasets. In one embodiment, determining that the given local dataset is an outlier dataset includes comparing the degree of outlierness of the given local dataset to a threshold, and determining that the degree of outlierness of the given local dataset exceeds the threshold. In an illustrative embodiment, the threshold can be set to 0.6. However, the threshold can be any suitable value in accordance with the embodiments described herein. In another embodiment, using a suitable variable k, a top-k outlier ranking can be returned.

At block 560, one or more actions are implemented based on the determination.

For example, the one or more actions can include building a machine learning model pertaining to medical science at block 570-1. In one embodiment, the machine learning model can include a logistic regression model. For example, the clinical researcher can have access to the datasets stored on the decentralized private network, and the clinical researcher can build the machine learning model by implementing data quality ranking to utilize one or more high quality datasets.

For example, assume that a clinical researcher wants to research arteriosclerotic cardiovascular disease (ASCVD). The clinical researcher would like to build a machine learning model for predicting in-hospital MACE (major adverse cardiac event) risk of ASCVD patients. To do this, the clinical researcher can collect RWD from at least one medical entity (e.g., hospital). However, the clinical researcher wants to avoid collecting RWD from every medical entity because (1) some datasets can have poor quality (e.g., due to scrivener error or poor information systems) and (2) collecting datasets can be costly and good research needs high quality datasets. The embodiments described herein can allow the clinical researcher to detect poor quality datasets as outlier datasets.

As another example, the one or more actions can include triggering a notification to the site(s) corresponding to the outlier dataset(s) at block 570-2. The suspicious site(s) can then modify their datasets by, e.g., uploading new version of datasets with improved data quality, thereby the collection of data stored on the decentralized private network.

As yet another example, the one or more actions can include transmitting and displaying one or more suitable datasets on a computing device of a doctor for use in treating a patient at block 570-3. The one or more suitable datasets can include one or more of the datasets stored on the decentralized private network that are not determined to be poor quality or outlier datasets. Further details regarding block 570-3 are described below with reference to FIG. 6.

Figure 6:
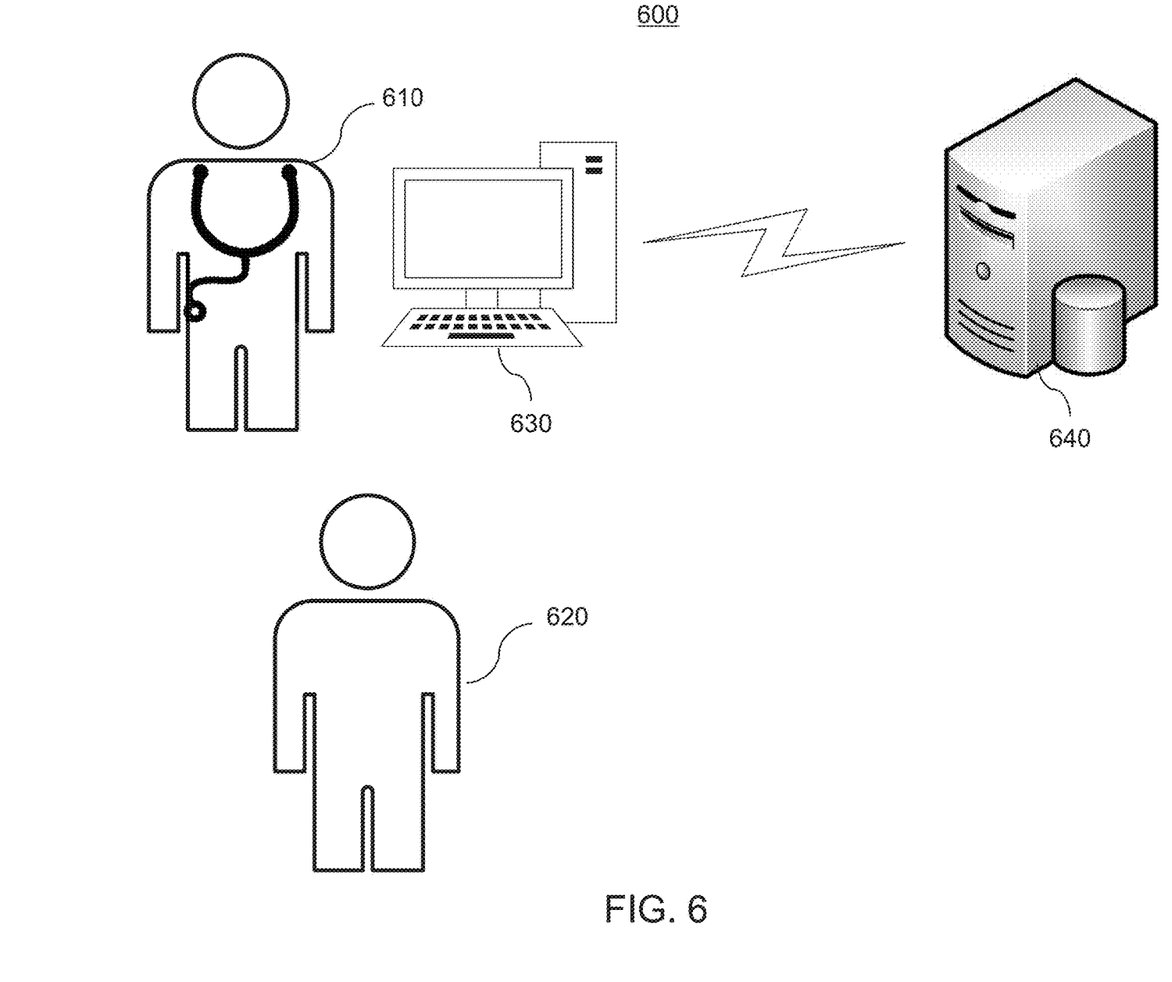
FIG. 6 is a block diagram of a system for displaying medical data for treating a patient, in accordance with an embodiment of the present invention.

With reference to FIG. 6, a block diagram is provided illustrating a system 600 for displaying medical data for treating a patient.

As shown, a doctor 610 is treating a patient 620 for an illness. In treating the patient 620, the doctor 610 can consult a computing device 630 to obtain data pertaining to, e.g., medications and/or medical devices that have been shown to be effective in treating the illness. Although the computing device 630 is shown in this illustrative example as a desktop computer, the computing device 630 can be any suitable computing device in accordance with the embodiments described herein (e.g., laptop, mobile device). More specifically, the doctor 610 can access RWD and/or RWE via server 640 (e.g., a database server). The doctor 610 can obtain the highest quality available data related to medications shown to treat the illness via the server 640 in accordance with the embodiments described herein.

Having described preferred embodiments of systems and methods for decentralized privacy-preserving clinical data evaluation (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed:

1. A system for decentralized privacy-preserving clinical data evaluation, comprising:
 a plurality of sites of a decentralized private network, the plurality of sites being associated with respective medical entities, wherein each of the plurality of sites includes:
  a local database maintaining a local dataset including a partition of a clinical dataset;
  chaincode configured to communicate with an ordering service of the decentralized private network and implement model construction and dataset score computing; and
  a ledger maintaining a local model trained based on the local dataset to preserve anonymity of the corresponding medical entity;
 a memory device for storing program code; and
 at least one processor device operatively coupled to the memory device and configured to execute program code stored on the memory device to:
  for each of the local datasets, evaluate the local dataset using each of the local models to obtain one or more features related to a degree of outlierness for each of the plurality of sites, wherein one or more features related to the degree of outlierness is calculated from an error matrix E, the error matrix E being calculated based on the local models;
determine at least one outlier dataset based on the one or more features by comparing the degree of outlierness for the local datasets to a threshold, the degree of outlierness including a first distribution of errors $D_1$, a second distribution of errors $D_2$, a Max, a Min, an Average, and Sum for each of the plurality of sites; and
implement one or more actions based on the determination.

2. The system of claim 1, further comprising and error simulation and modeling service of the decentralized private network in communication with the ordering service and configured to:
select a reference model from a model pool based on a target model; and
perform error simulation and classifier training based on the reference model.

3. The system of claim 2, wherein the error simulation and modeling service is configured to perform the error simulation and classifier training based on the reference model by:
obtaining a reference error matrix based on the reference model; and
training a classifier based on the reference error matrix.

4. The system of claim 2, wherein each of the plurality of sites is configured to train its local model based on the reference model and its local dataset, and submit its local model to its ledger for the evaluation.

5. The system of claim 1, wherein the at least one processor device is configured to evaluate the local dataset for all of the local models by calculating an error matrix across the plurality of sites.

6. The system of claim 1, wherein the at least one processor device is configured to identify the one or more outlier datasets by using the classifier to classify which of the local datasets are outlier datasets.

7. The system of claim 1, wherein the decentralized private network includes a blockchain network.

8. A computer-implemented method for decentralized privacy-preserving clinical data evaluation, comprising:
obtaining, from each of a plurality of sites of a decentralized private network, a local model trained based on a local dataset including a partition of a clinical dataset, the plurality of sites being associated with respective medical entities, wherein each of the plurality of sites includes:
a local database maintaining its local dataset;
chaincode configured to communicate with an ordering service of the decentralized private network and implement model construction and dataset score computing; and
a ledger maintaining the local model to preserve anonymity of the corresponding medical entity;
for each of the local datasets, evaluating the local dataset using each of the local models to obtain one or more features related to a degree of outlierness for each of the plurality of sites, wherein one or more features related to the degree of outlierness is calculated from an error matrix E, the error matrix E being calculated based on the local models;
determining at least one outlier dataset based on the one or more features by comparing the degree of outlierness for the local datasets to a threshold, the degree of outlierness including a first distribution of errors $D_1$, a second distribution of errors $D_2$, a Max, a Min, an Average, and Sum for each of the plurality of sites; and
implementing one or more actions based on the determination.

9. The method of claim 8, further comprising:
selecting, by an error simulation and modeling service of the decentralized private network in communication with the ordering service, a reference model from a model pool based on the target model; and
performing, by the error simulation and modeling service, error simulation and classifier training based on the reference model.

10. The method of claim 9, wherein performing the error simulation and classifier training based on the reference model further includes:
obtaining a reference error matrix based on the reference model; and
training a classifier based on the reference error matrix.

11. The method of claim 9, wherein a given one of the plurality of sites is configured to train its local model based on the reference model and its local dataset, and submit its local model to its ledger for the evaluation.

12. The method of claim 8, wherein evaluating the local dataset for all of the local models further includes calculating an error matrix across the plurality of sites.

13. The method of claim 8, wherein identifying the one or more outlier datasets further includes using the classifier to classify which of the local datasets are outlier datasets.

14. The method of claim 8, wherein the decentralized private network includes a blockchain network.

15. A computer program product comprising a non-transitory computer readable storage medium having program instructions embodied therewith, the program instructions executable by a computer to cause the computer to perform a method for decentralized privacy-preserving clinical data evaluation, the method performed by the computer comprising:
obtaining, from each of a plurality of sites of a decentralized private network, a local model trained based on a local dataset including a partition of a clinical dataset, the plurality of sites being associated with respective medical entities, wherein each of the plurality of sites includes:
a local database maintaining its local dataset;
chaincode configured to communicate with an ordering service of the decentralized private network and implement model construction and dataset score computing; and
a ledger maintaining the local model to preserve anonymity of the corresponding medical entity;
for each of the local datasets, evaluating the local dataset using each of the local models to obtain one or more features related to a degree of outlierness for each of the plurality of sites, wherein one or more features related to the degree of outlierness is calculated from an error matrix E, the error matrix E being calculated based on the local models;
determining at least one outlier dataset based on the one or more features by comparing the degree of outlierness for the local datasets to a threshold, the degree of outlierness including a first distribution of errors $D_1$, a second distribution of errors $D_2$, a Max, a Min, an Average, and Sum for each of the plurality of sites; and
implementing one or more actions based on the determination.

16. The computer program product of claim 15, further comprising:
    selecting; by an error simulation and modeling service of the decentralized private network in communication with the ordering service, a reference model from a model pool based on the target model; and
    performing, by the error simulation and modeling service, error simulation and classifier training based on the reference model, including obtaining a reference error matrix based on the reference model, and training a classifier based on the reference error matrix.

17. The computer program product of claim 16, wherein a given one of the plurality of sites is configured to train its local model based on the reference model and its local dataset, and submit its local model to its ledger for the evaluation.

18. The computer program product of claim 15, wherein evaluating the local dataset for all of the local models further includes calculating an error matrix across the plurality of sites.

19. The computer program product of claim 15, wherein identifying the one or more outlier datasets further includes using the classifier to classify which of the local datasets are outlier datasets.

20. The computer program product of claim 15, wherein the decentralized private network includes a blockchain network.

* * * * *